(12) United States Patent
Singh et al.

(10) Patent No.: US 10,696,636 B2
(45) Date of Patent: Jun. 30, 2020

(54) PROCESS FOR THE PREPARATION OF HIV INTEGRASE INHIBITORS

(71) Applicant: Lupin Limited, Mumbai (IN)

(72) Inventors: Girij Pal Singh, Pune (IN); Dhananjai Shrivastava, Pune (IN); Harishchandra Sambhaji Jadhav, Pune (IN); Pramod Sudhakar Utekar, Pune (IN); Digambar Yashwant Salunke, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 205 days.

(21) Appl. No.: 16/063,732

(22) PCT Filed: Dec. 15, 2016

(86) PCT No.: PCT/IB2016/057638
§ 371 (c)(1),
(2) Date: Jun. 19, 2018

(87) PCT Pub. No.: WO2017/109649
PCT Pub. Date: Jun. 29, 2017

(65) Prior Publication Data
US 2020/0172487 A1 Jun. 4, 2020

(30) Foreign Application Priority Data
Dec. 21, 2015 (IN) .......................... 4792/MUM/2015

(51) Int. Cl.
*C07D 213/803* (2006.01)

(52) U.S. Cl.
CPC ...... *C07D 213/803* (2013.01); *C07B 2200/13* (2013.01)

(58) Field of Classification Search
None
See application file for complete search history.

(56) References Cited

FOREIGN PATENT DOCUMENTS

| EP | 2602260 A1 | 6/2013 |
|---|---|---|
| WO | 2015/110897 A2 | 7/2015 |
| WO | 2015/177537 A1 | 11/2015 |

OTHER PUBLICATIONS

PCT International Search Report & Written Opinion dated Mar. 3, 2017, Application No. PCT/IB2016/057638.

*Primary Examiner* — Zinna Northington Davis
(74) *Attorney, Agent, or Firm* — The Dobrusin Law Firm, PC

(57) ABSTRACT

The present invention provides compound of formula (XVII), wherein P is hydroxyl protecting group; R2 and R3 are independently lower alkyl or R2 and R3 can be alkyl and joined to form a 5-, 6- or 7-membered ring; R4 is lower alkyl, and process for its preparation.

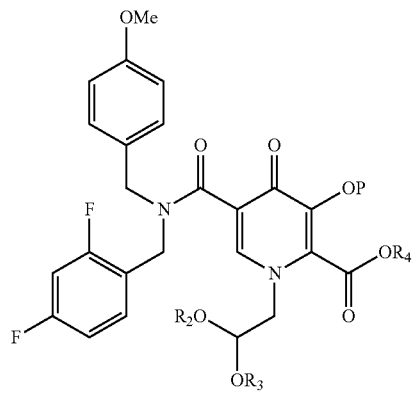

10 Claims, 1 Drawing Sheet

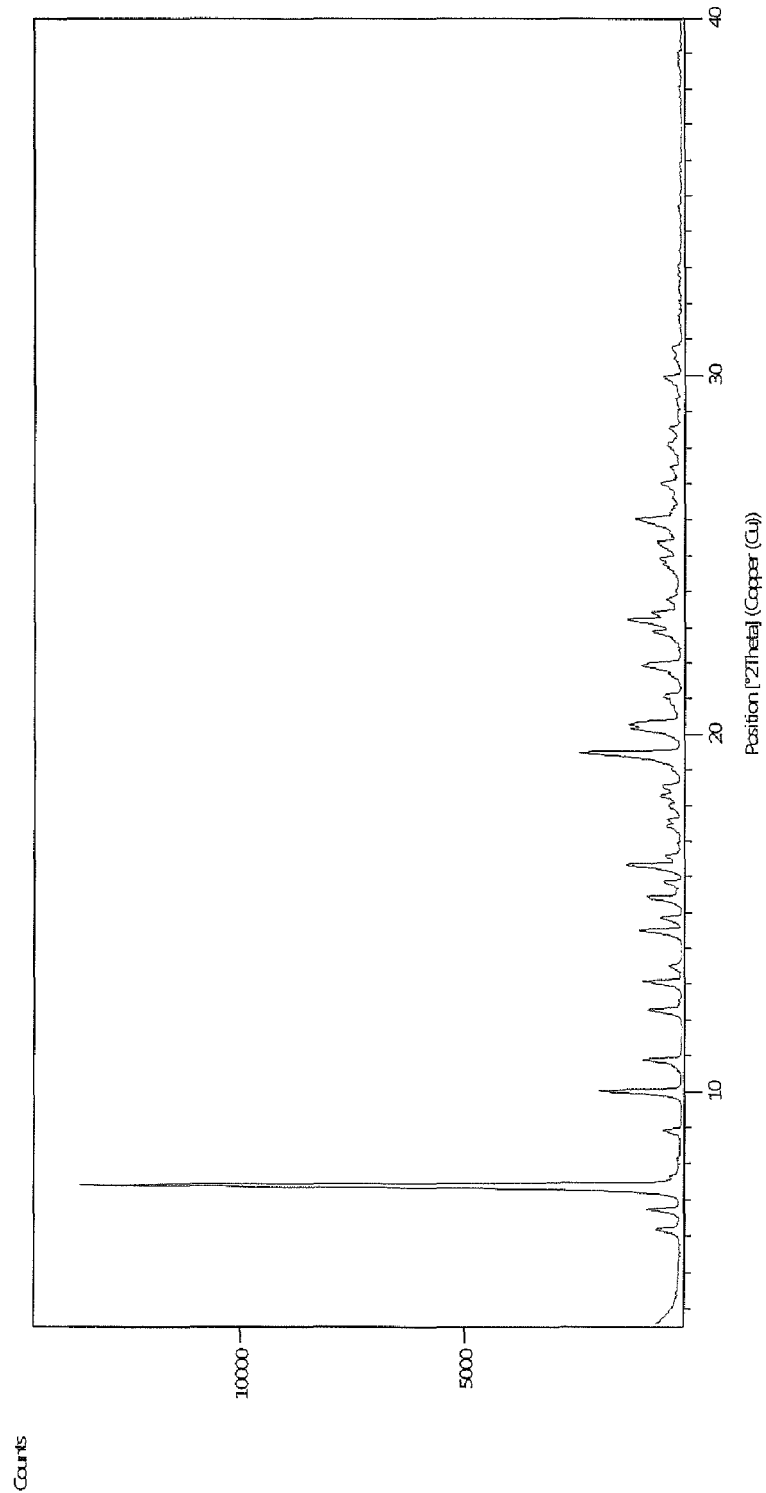

PROCESS FOR THE PREPARATION OF HIV INTEGRASE INHIBITORS

FIELD OF THE INVENTION

The present invention relates to process for the preparation of HIV integrase inhibitors.

BACKGROUND OF THE INVENTION

Polycyclic carbamoylpyridone derivatives having HIV integrase inhibitory activity are described in PCT application WO 2006/116764.

Dolutegravir (I) and cabotegravir (II) are polycyclic carbamoylpyridone derivatives. Dolutegravir (I) is used against HIV infections as a single drug or fixed-dose combination with abacavir sulphate and lamivudine under the trade names Tivicay® and Triumeq® respectively. These commercial products contain dolutegravir as its sodium salt. It is chemically known as (4R,12aS)-9-{[(2,4-difluorophenyl) methyl]carbamoyl}-4-methyl-6,8-dioxo-3,4,6,8,12,12a-hexahydro-2H-pyrido[1',2':4,5]pyrazino[2,1-b][1,3]oxazin-7-olate having chemical structure of formula I.

Cabotegravir (II) is in phase II clinical trials and is chemically known as (3S,11aR)—N-[(2,4-difluorophenyl) methyl]-6-hydroxy-3-methyl-5,7-dioxo-2,3,5,7,11,11a-hexahydrooxazolo-[3,2-a]pyrido[1,2-d]pyrazine-8-carboxamide having following chemical structure of formula II.

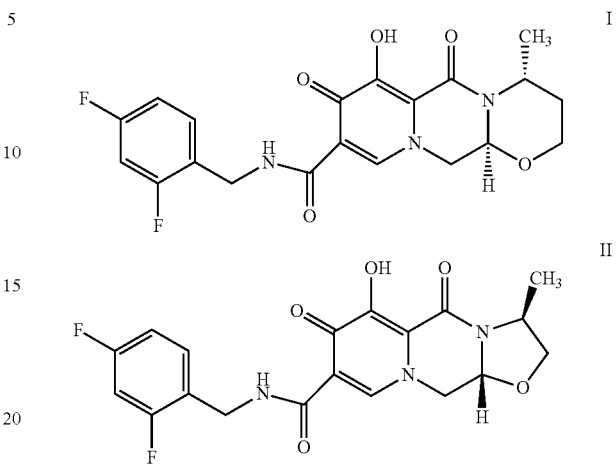

The PCT application WO 2006/116764 describes following process for the preparation of compound of formula I, compound of formula II and compound of formula III.

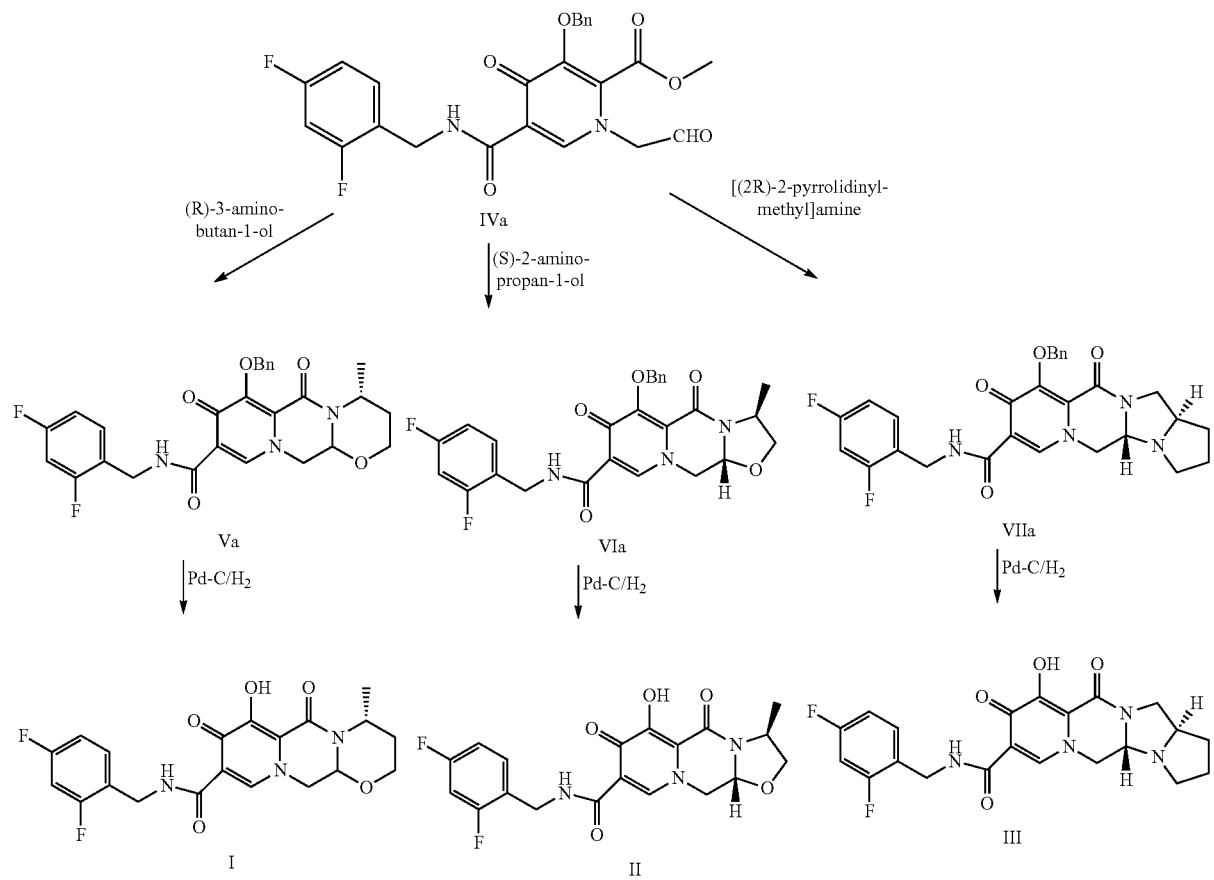

The U.S. Pat. No. 8,865,907 describes following processes for the preparation of intermediates for the synthesis of compound of formula I, compound of formula II and compound of formula III.

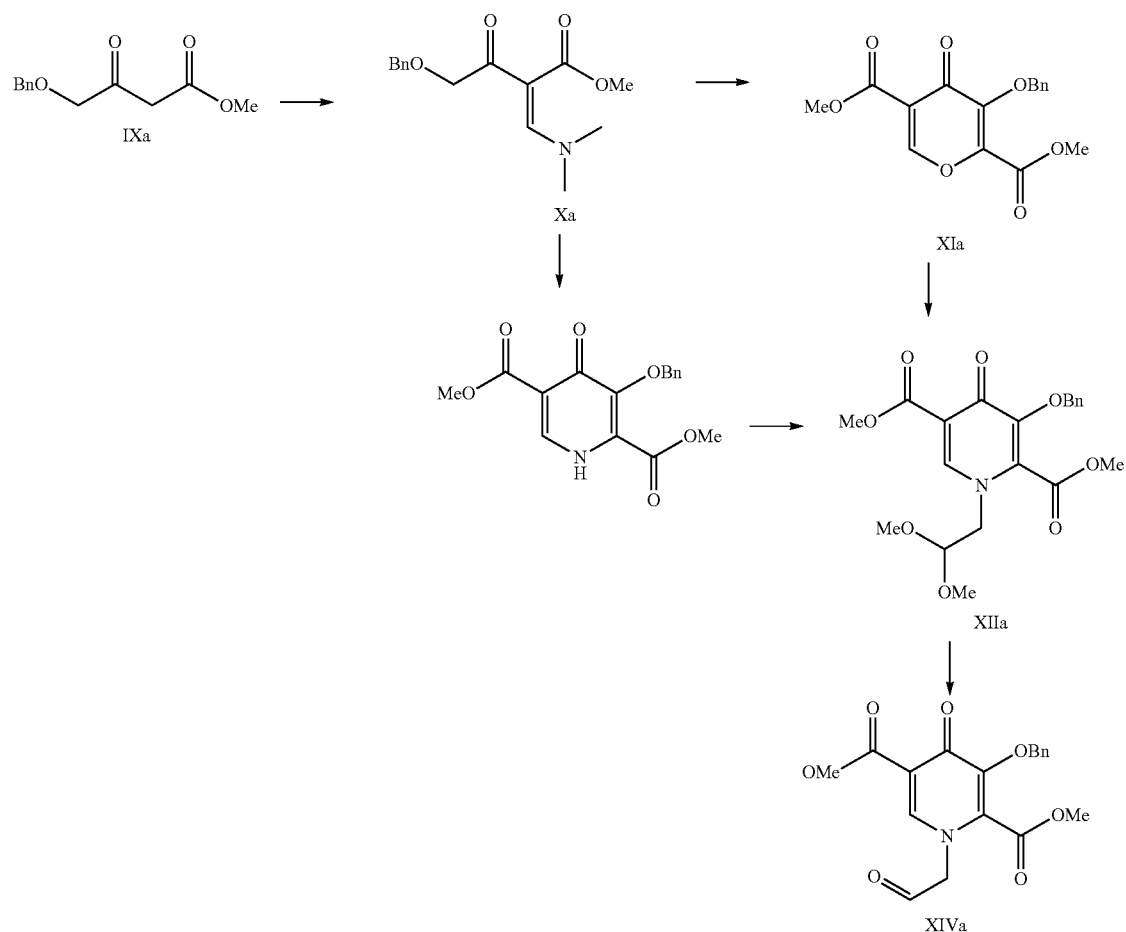
The U.S. Pat. No. 8,889,877 describes following process for the preparation of intermediates for the synthesis of compound of formula I, compound of formula II and compound of formula III.
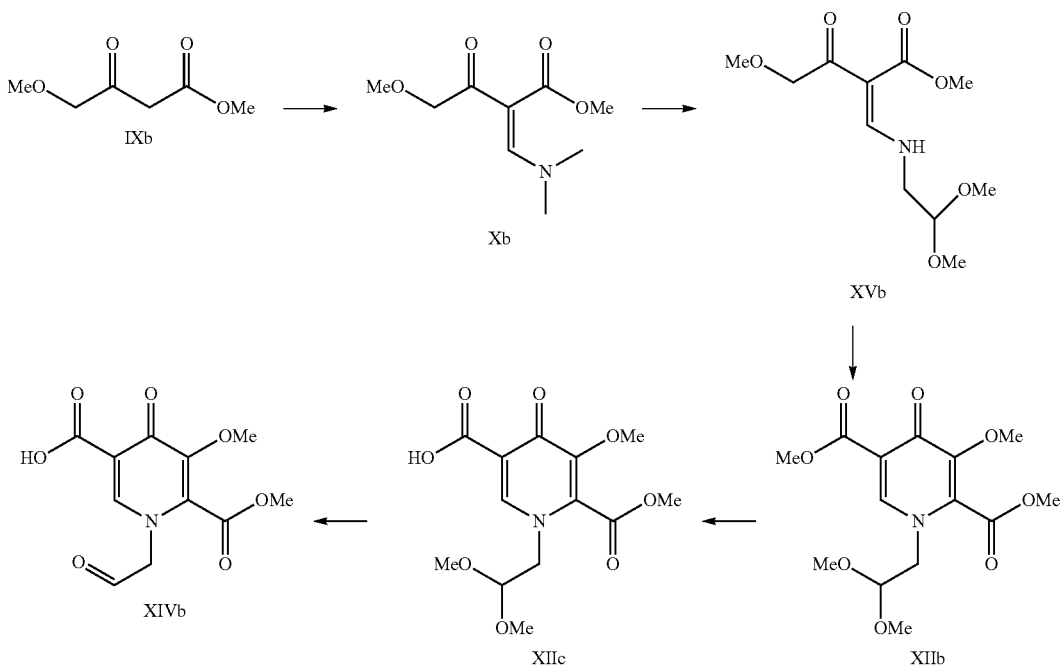

Various processes for the preparation of polycyclic carbamoylpyridone derivatives are described in U.S. Pat. Nos. 8,624,023, 8,669,362 and US 20150038702.

SUMMARY OF THE INVENTION

The present invention provides a process for the preparation of a compound of formula IV

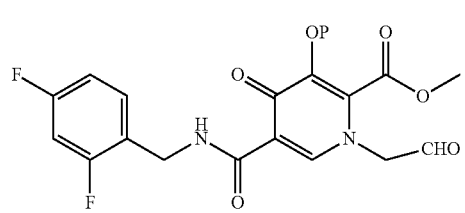

IV wherein P is hydroxyl protecting group,
comprising reacting a compound of formula XII

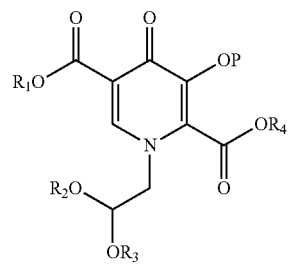

XII wherein P is hydroxyl protecting group;
R1 is H or lower alkyl;
R2 and R3 are independently lower alkyl or R2 and R3 can be alkyl and joined to form a 5-, 6- or 7-membered ring;
R4 is lower alkyl,
with a compound of formula XVI

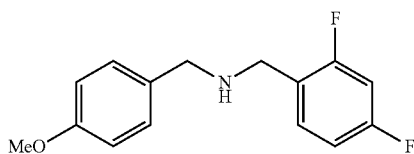

XVI to form a compound of formula XVII

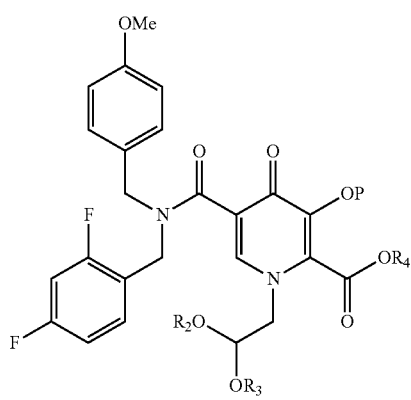

XVII and converting a compound of formula XVII to a compound of formula IV.

The present invention further relates to converting the compound of formula IV to compound of formula I, or compound of formula II, or compound of formula III.

The present invention further provides compound of formula XVII

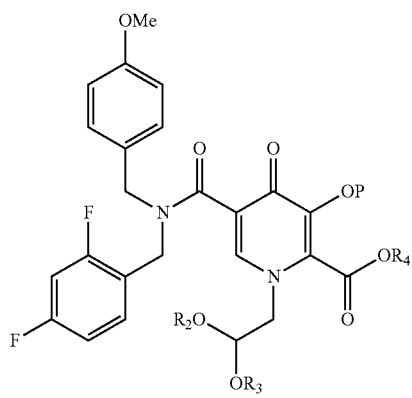

XVII wherein each symbol is as defined above.

The present invention further provides a compound of formula XVIIa

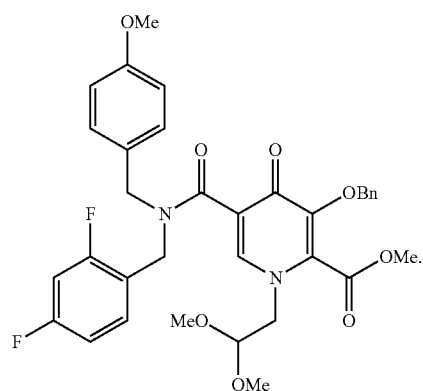

XVIIa

The present invention further provides a crystal form of a compound of formula XVIIa

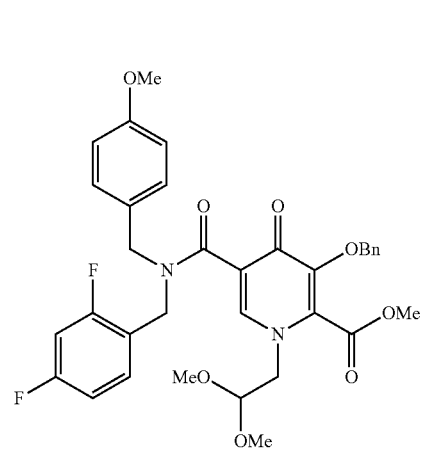

XVIIa which has peaks in a powder X-ray diffraction spectrum at diffraction angle (2θ): 7.4°±0.2°, 10.0°±0.2°, 19.4°±0.2° and 21.9°±0.2°.

BRIEF DESCRIPTION OF THE FIGURE

FIG. 1—Powder X-ray diffraction spectrum of compound of formula XVIIa.

DETAILED DESCRIPTION OF THE INVENTION

Hereinafter, the terms used in the present specification are described.

Hydroxy protecting group may be selected from groups known to those skilled in the art, including protecting groups disclosed in Greene, Theodora W.; Wuts, Peter G. M. Protective Groups in Organic Synthesis. 3rd Ed. (1999).

Examples of a hydroxy protecting group (P) include lower alkyl, aralkyl (e.g. benzyl), acyl (e.g. acetyl, pivaloyl, benzoyl), alkoxyalkyl (e.g. methoxymethyl, methoxyethyl), lower alkylsulfonyl (e.g. methanesulfonyl), arylsulfonyl (e.g. benzenesulfonyl, toluenesulfonyl), alkoxycarbonyl (e.g. methoxycarbonyl) and the like.

The term "lower alkyl" encompasses linear or branched alkyl having 1 to 6 carbon atoms, preferably 1 to 4 carbon atoms, most preferably 1 or 2 carbon atoms. Examples thereof include methyl, ethyl, n-propyl, isopropyl, n-butyl, isobutyl, sec-butyl, tert-butyl, n-pentyl, isopentyl, neopentyl, hexyl, isohexyl. Examples of preferred embodiments of "lower alkyl" include methyl, ethyl, n-propyl, isopropyl, n-butyl, isobutyl, sec-butyl, tert-butyl, and n-pentyl. Examples of more preferred embodiments thereof include methyl, ethyl, n-propyl, isopropyl, and tert-butyl.

In one embodiment, the present invention provides a process for preparation of compound of formula XVII by reacting compound of formula XII with compound of formula XVI as shown below

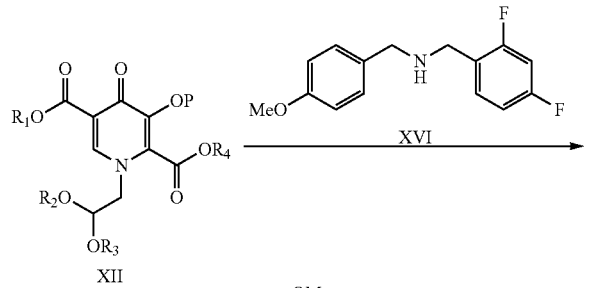

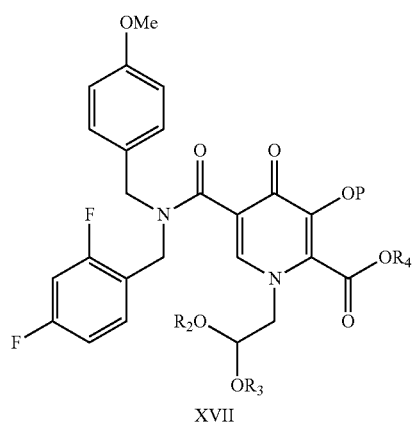

wherein each symbol is as defined above.

The compound of formula XII and XVI may be commercially available reagent or can be obtained by methods known in the literature.

When $R_1$ is hydrogen, the reaction can be carried under coupling conditions using coupling agent.

The coupling agent may be selected from pivaloyl chloride, isobutyl chloroformate carbonyldiimidazole, o-benzotriazole-1-yl-1,1,3,3-tetramethyluronium tetrafluoroborate, 2-(1H-benzotriazole-1-yl)-1,1,3,3-tetramethyluronium, benzotriazole-1-yl-oxy-tris(dimethylamino)phosphonium, benzotriazole-1-yl-oxy-tris-(pyrrolidino)phosphonum, bromo-tris-pyrrolidino-phosphoniumhexaflurophosphate, tris (pyroolidino)phosphonium hexaflurophosphate, ethyl cyanoglyoxylate-2-oxime, O-(6-chloro-1-hydrocibenzotriazol-1-yl)-1,1,3,3-tetramethyluronium tetrafluoroborate, 2-(1H-7-azabenzotriazol-1-yl)-1,1,3,3-tetramethyl uronium hexafluorophosphate and 1-cyano-2-ethoxy-2-oxoethydenminooxy)dimethylamino-morpholion-carbenium hexafluorophosphate (COMU) and mixture thereof.

The reaction is carried out in presence of an organic base selected from triethylamine, N-methylmorpholine, diisopropylethylamine, N,N'-dimethylpiperazine, N-methylpiperidine, pyridine or mixture thereof.

The reaction is carried out in an organic solvent selected from dichloromethane, ethyl acetate, tetrahydrofuran, dimethyl formamide, toluene, acetonitrile, acetone and mixture thereof. The reaction is carried out at a temperature of −30 to 80° C.

The COOR1 of compound XII is converted to —COOH by reacting with lithium hydroxide in C1-C4 alcohol such as methanol, ethanol, isopropanol, butanol. The reaction is carried out at a temperature of 0° C. to 80° C.

The compound XVII may be isolated by a general purification method such as extraction, distillation, column chromatography, crystallization.

In another embodiment, the present invention provide a compound of formula XVII

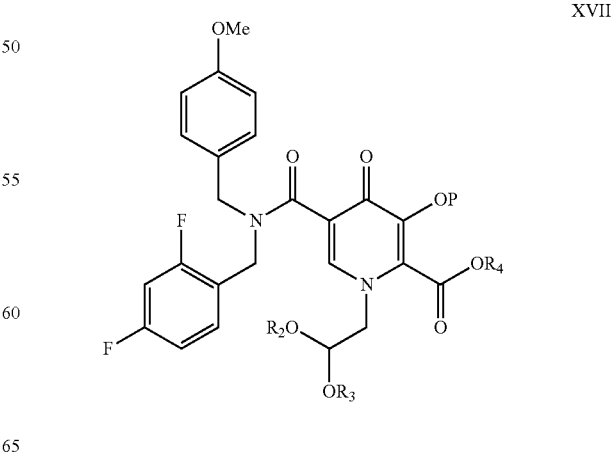

wherein each symbol is as defined above.

In yet another embodiment, the present invention provide a compound of formula XVIIa

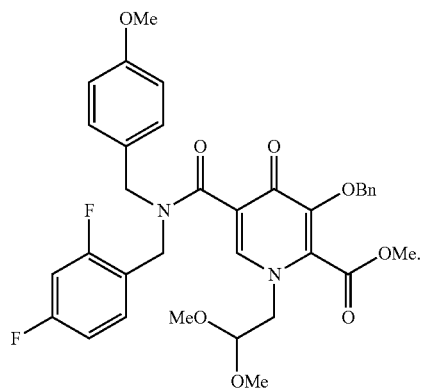

XVIIa

In another embodiment, the present invention provide a crystal form of a compound of formula XVIIa

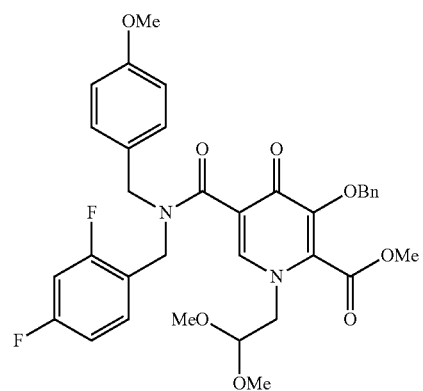

XVIIa which has peaks in a powder X-ray diffraction spectrum at diffraction angle (2θ): 7.4°±0.2°, 10.0°±0.2°, 19.4°±0.2° and 21.9°±0.2°. The powder X-ray diffraction spectrum of compound of formula XVIIa is depicted in FIG. 1.

In another embodiment, the present invention provides a process for preparation of compound of formula IV by reacting compound of formula XVII as shown below

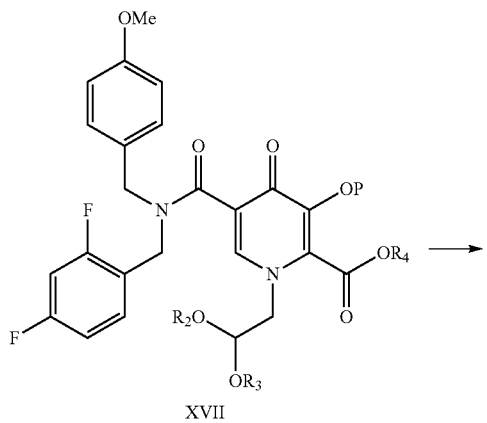

XVII

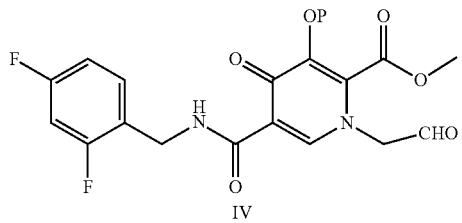

IV wherein each symbol is as defined above.

The reaction can be carried out with acetic acid and a catalytic amount of a strong protic acid in suitable solvent such as acetonitrile. The strong protic acid may be selected from methanesulfonic acid, toluene sulfonic acid, sulfuric acid, hydrochloric acid and formic acid. The reaction is carried out at a temperature of 0° C. to 100° C.

The compound of formula IV may be isolated by a general purification method such as extraction, distillation, column chromatography, crystallization. Alternatively, the compound of formula IV may be directly converted to compound of formula I, or compound of formula II, or compound of formula III.

The process of the present invention further comprises reacting compound of formula IV

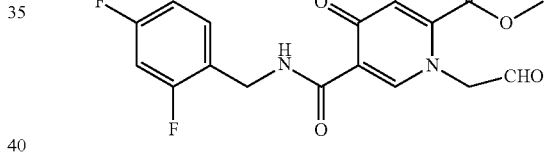

IV wherein P is hydroxyl protecting group;

with (R)-3-amino-butan-1-ol, or (S)-2-amino-propan-1-ol, or [(2R)-pyrrolidinylmethyl] amine to obtain a compound of formula V, or compound of formula VI, or compound of formula VII,

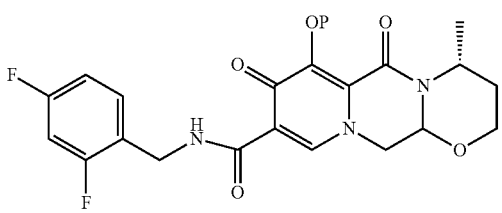

V

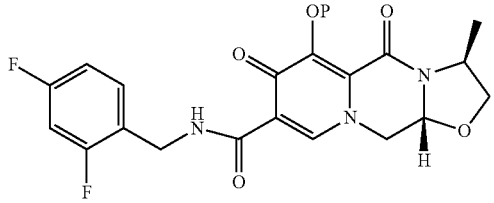

VI

-continued

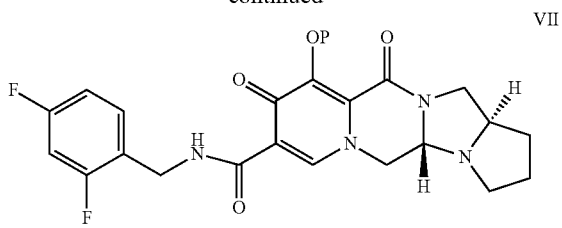

and deprotecting hydroxyl protecting group to obtain a compound of formula I, or compound of formula II, or compound of formula III respectively

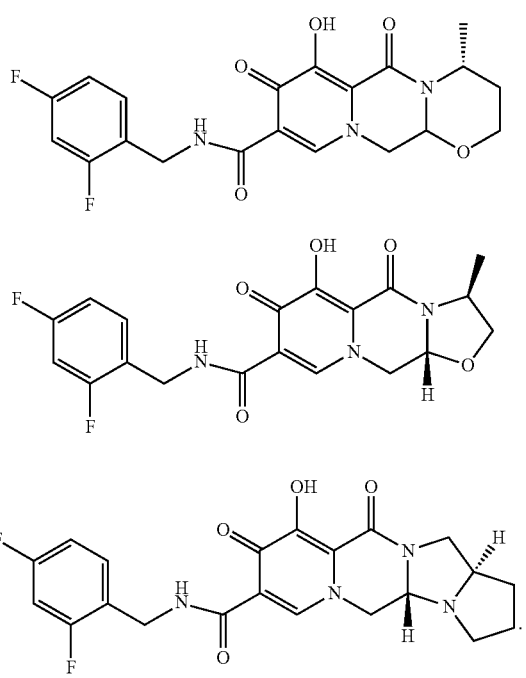

The conversion of compound of formula IV to compound of formula I, or compound of formula II, or compound of formula III may be carried out by the methods known in the art.

The compound of formula I, or compound of formula II, or compound of formula III may be converted to its pharmaceutically acceptable salts by the methods known in the art.

Pharmaceutically acceptable salts include, alkali metal salts such as sodium or potassium; alkaline-earth metal salts such as calcium or magnesium.

The present invention is described in the following examples, however it should be noted that the scope of present invention is not limited by the examples.

EXPERIMENTAL

Example 1

Preparation of 2,4-difluoro-N-[(4-methoxyphenyl) methyl]-benzenemethanamine (XVI)

Anisaldehyde (47 g, 0.35 mol) and 2,4-difluorobenzylamine (50 g, 0.35 mol) in toluene (250 ml) were stirred at 120-130° C. for 6 hours. Toluene was recovered under reduced pressure and methanol (250 ml) was added to the residue. Sodium borohydride (52 g, 1.4 mol) was added at 0-10° C. and the reaction mixture was stirred under nitrogen for 12 hours. Methanol was distilled out under reduced pressure and ethyl acetate (200 ml) was added. The mixture was extracted with water (200 ml) and the aqueous layer was acidified with 10% HCl. The solid was filtered and washed with ethyl acetate. Yield: 59 g.

Mass (m/z): 264.2 $(M+1)^+$.

Example 2

Preparation of Compound XIIa [XII: P=—CH$_2$Ph; R1, R2, R3 and R4=CH$_3$]

A mixture of ethyl 4-benzoxyacetoacetate (10 g, 0.04 mol) and dimethyl formamide dimethylacetal (20 g, 0.16 mol) in toluene (100 ml) was stirred at 20-30° C. for 1 hour. Aminoacetaldehyde dimethyl acetal (17.8 g, 0.16 mol) was added and the mixture was stirred at 20-30° C. for 1 hour. The mixture was extracted with water (100 ml) and the organic layer was washed with brine solution. The solvent was distilled off and methanol (50 ml) was added to the residue. Dimethyl oxalate (10 g, 0.08 mol) was added and the mixture was cooled to 5-10° C. Sodium methoxide solution (25%, 13.7 g, 0.06 mol) was added at 5-10° C. and the mixture was heated at 40-45° C. for 20 hours. The reaction mixture was cooled to 5-10° C. Water (50 ml) and 10% HCl solution (50 ml) were added. The mixture was extracted with ethyl acetate (100 ml) and the solvent is distilled to get oily residue.

Mass (m/z): 406.2 $(M+1)^+$.

Example 3

Preparation of Compound XIId [XII: P=—CH$_2$Ph; R1=H; R2, R3 and R4=CH$_3$]

Compound XIIa [XII: P=—CH$_2$Ph; R1, R2, R3 and R4=CH$_3$] (25 g, 0.0617 mol) was dissolved in methanol (250 ml). Lithium hydroxide (2.2 g,) was added 0-10° C. and the mixture was stirred at 25-30° C. for 6 hours. The solvent was recovered under reduced pressure and ethyl acetate (150 ml) was added to the residue. The mixture was extracted with water (150 ml) and the aqueous layer was acidified with 5% HCl solution (100 ml). The aqueous layer was extracted with ethyl acetate (150 ml) and the organic layer was washed with brine solution. The solvent was recovered under reduced pressure to get compound XIId as oil. Yield: 16 g.

Mass (m/z): 392.2 $(M+1)^+$.

Example 4

Preparation of Compound XVIIa

Compound XIId [XII: P=—CH$_2$Ph; R1=H; R2, R3 and R4=CH$_3$] (16 g, 0.04 mol) was dissolved in dichloromethane (80 ml). Triethylamine (4.5 g, 0.045 mol) and pivaloyl chloride (5.4 g, 0.045 mol) were added at 0-10° C. and the mixture was stirred at the same temperature for an hour. Compound XVI (13 g, 0.05 mol) was added and the mixture was stirred at 20-30° C. for 3 hours. Water (80 ml) was added at 0-10° C. and the organic layer was separated. Organic layer was washed with saturated brine solution and the solvent was recovered under reduced pressure. The residue was crystallized with methyl tertiary-butyl ether (32 ml). Yield: 14 g (yellow solid).

Mass (m/z): 637.3 (M+1)$^+$.

The powder X-ray diffraction spectrum of compound of formula XVIIa is depicted in FIG. 1.

Example 5

Preparation of Compound Va

Compound XVIIa (5 g, 0.0078 mol) was dissolved in acetonitrile (50 ml). Acetic acid (2.3 g, 0.04 mol) and methane sulfonic acid (0.2 g, 0.002 mol) were added at 20-30° C. and the mixture was heated at 80-90° C. for 24 hours. (R)-3-amino butan-1-ol (1.0 g, 0.01 mol) was added and the mixture was stirred at 80-85° C. for 24 hours. The solvent was distilled off and water (50 ml) was added. The mixture was extracted with dichloromethane (50 ml) and the organic layer was washed with 10% brine solution. The solvent was recovered under reduced pressure to get compound Va as oil. Yield: 3 g.

Example 6

Preparation of Dolutegravir (I)

A mixture of compound Va (2 g, 0.003 mol) and 10% Pd—C (0.2 g) in methanol (20 ml) was stirred at 20-30° C. for 2 hours under hydrogen atmosphere. The mixture was filtered and the solvent was distilled off. Isopropanol (20 ml) was added to the residue and the solid was filtered. Yield: 0.2 g

The invention claimed is:

1. A process for the preparation of a compound of formula IV

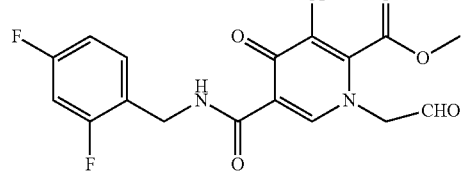

IV wherein P is hydroxyl protecting group,
comprising reacting a compound of formula XII

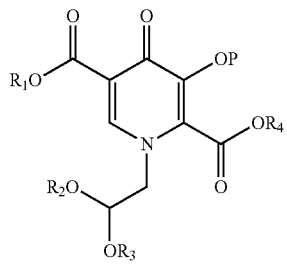

XII wherein P is hydroxyl protecting group;

R1 is H or lower alkyl;

R2 and R3 are independently lower alkyl or R2 and R3 can be alkyl and joined to form a 5-, 6- or 7-membered ring;

R4 is lower alkyl, with a compound of formula XVI

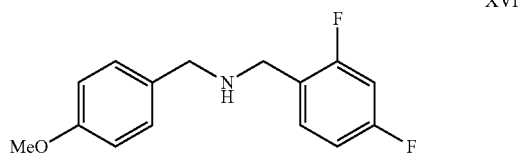

XVI to form a compound of formula XVII

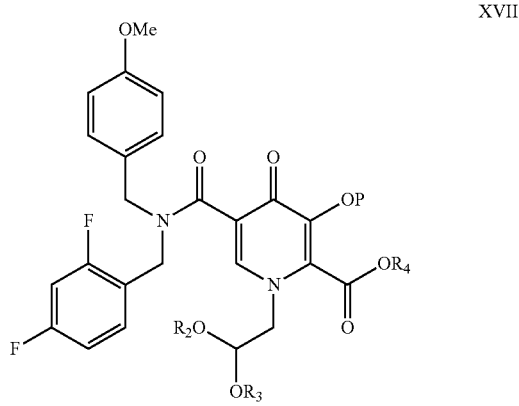

XVII and converting a compound of formula XVII

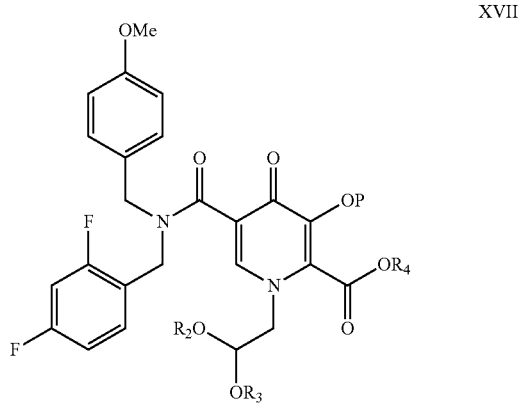

XVII to a compound of formula IV

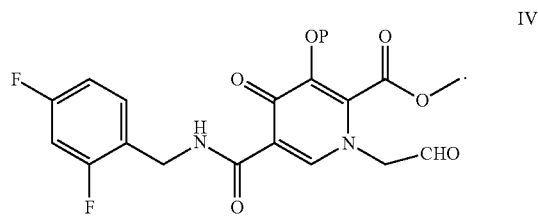

IV

2. The process of claim 1 wherein reaction of compound of formula XII with a compound of formula XVI is carried out under coupling conditions using coupling agent.

3. The process of claim 2 wherein the coupling agent is selected from pivaloyl chloride, isobutyl chloroformate carbonyldiimidazole, o-benzotriazole-1-yl-1,1,3,3-tetramethyluronium tetrafluoroborate, 2-(1H-benzotriazole-1-yl)-1,1,3,3-tetramethyluronium, benzotriazole-1-yl-oxy-tris (dimethylamino)phosphonium, benzotriazole-1-yl-oxy-tris-(pyrrolidino)phosphonum, bromo-tris-pyrrolidino-phosphoniumhexaflurophosphate, tris(pyroolidino) phosphonium hexafluorophosphate, ethyl cyanoglyoxylate-2-oxime, O-(6-chloro-1-hydrocibenzotriazol-1-yl)-1,1,3,3-tetramethyluronium tetrafluoroborate, 2-(1H-7-azabenzotriazol-1-yl)-1,1,3,3-tetramethyl uronium hexafluorophosphate and 1-cyano-2-ethoxy-2-oxoethyden-minooxy)dimethylamino-morpholion-carbenium hexafluorophosphate (COMU) and mixture thereof.

4. The process of claim 1 wherein the conversion of a compound of formula XVII to a compound of formula IV is carried out with acetic acid and a catalytic amount of a strong protic acid in acetonitrile.

5. The process of claim 4 wherein the strong protic acid is selected from methanesulfonic acid, toluene sulfonic acid, sulfuric acid, hydrochloric acid and formic acid.

6. The process of claim 1 further comprises converting the compound of formula IV to compound of formula I, or compound of formula II, or compound of formula III.

7. The process of claim 6 wherein the process comprises reacting compound of formula IV

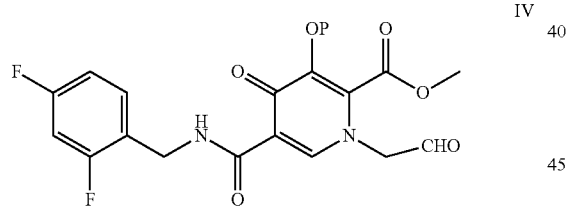

IV wherein P is hydroxyl protecting group;
with (R)-3-amino-butan-1-ol, or (S)-2-amino-propan-1-ol, or [(2R)-pyrrolidinylmethyl]amine to obtain a compound of formula V, or compound of formula VI, or compound of formula VII

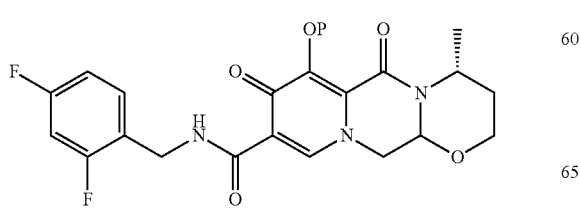

V

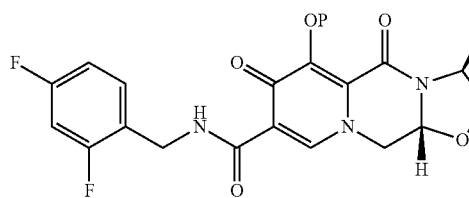

VI

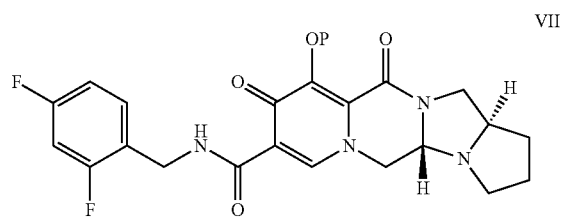

VII and deprotecting hydroxyl protecting group to obtain a compound of formula I, or compound of formula II, or compound of formula III, respectively

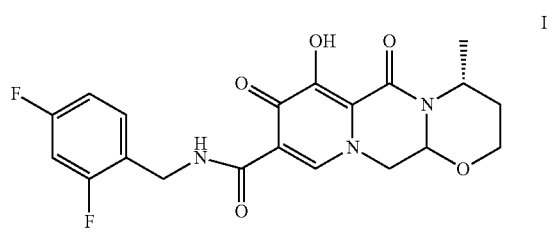

I

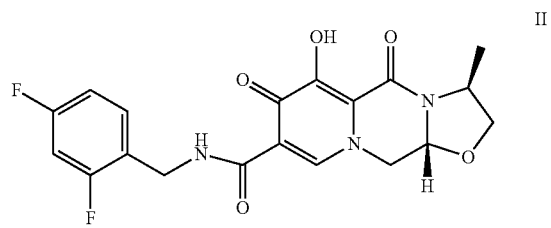

II

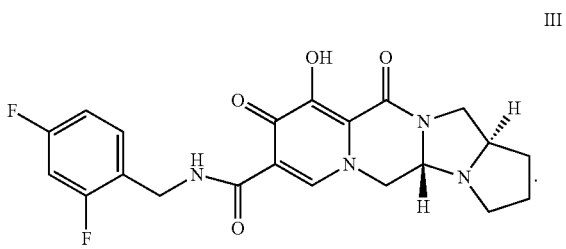

III

8. A compound of formula XVII

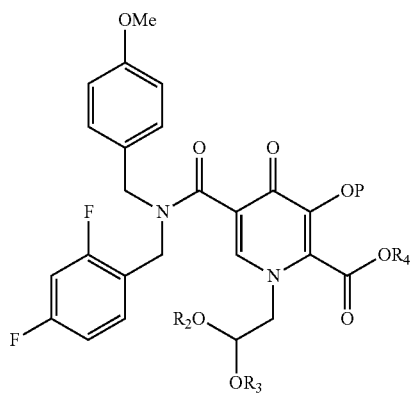

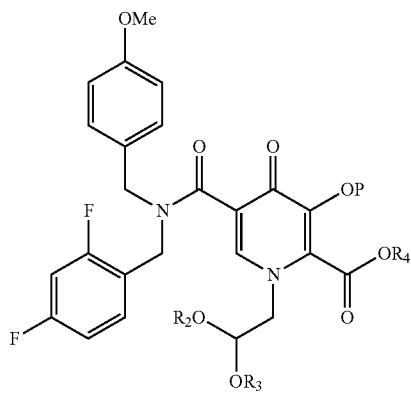

wherein P is hydroxyl protecting group;
R1 is H or lower alkyl; and
R2 and R3 are independently lower alkyl or R2 and R3 can be alkyl and joined to form a 5-, 6- or 7-membered ring.

9. A compound according to claim 8, of formula XVIIa

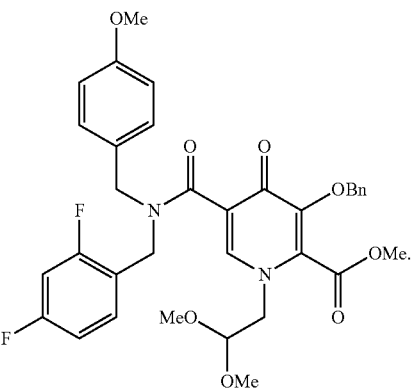

10. A crystal form of a compound of formula XVIIa of claim 9,

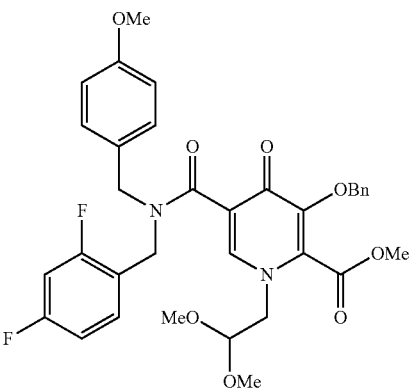

which has peaks in a powder X-ray diffraction spectrum at diffraction angle (2θ): 7.4°±0.2°, 10.0°±0.2°, 19.4°±0.2° and 21.9°±0.2°.

* * * * *

UNITED STATES PATENT AND TRADEMARK OFFICE
CERTIFICATE OF CORRECTION

PATENT NO. : 10,696,636 B2
APPLICATION NO. : 16/063732
DATED : June 30, 2020
INVENTOR(S) : Girij Pal Singh et al.

Page 1 of 1

It is certified that error appears in the above-identified patent and that said Letters Patent is hereby corrected as shown below:

In the Claims

Column 17, Lines 1-17 remove formula XVII

Signed and Sealed this
First Day of September, 2020

Andrei Iancu
*Director of the United States Patent and Trademark Office*